United States Patent
Kang et al.

(10) Patent No.: US 10,100,147 B2
(45) Date of Patent: Oct. 16, 2018

(54) ORGANIC ZINC CATALYST, PREPARATION METHOD THEREOF, AND METHOD OF PREPARING POLY(ALKYLENE CARBONATE) RESIN USING THE SAME

(71) Applicant: LG CHEM, LTD., Seoul (KR)

(72) Inventors: Seong Kyun Kang, Daejeon (KR); Sung-Kyoung Kim, Daejeon (KR); Jun Wye Lee, Daejoen (KR); Eun Kyoung Park, Daejeon (KR); Seung Young Park, Daejoen (KR); Hyeon Choi, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/303,349

(22) PCT Filed: Jun. 12, 2015

(86) PCT No.: PCT/KR2015/005951
§ 371 (c)(1),
(2) Date: Oct. 11, 2016

(87) PCT Pub. No.: WO2015/190874
PCT Pub. Date: Dec. 17, 2015

(65) Prior Publication Data
US 2017/0029563 A1 Feb. 2, 2017

(30) Foreign Application Priority Data

Jun. 13, 2014 (KR) .................. 10-2014-0072346
Jun. 13, 2014 (KR) .................. 10-2014-0072347
Jun. 11, 2015 (KR) .................. 10-2015-0082527

(51) Int. Cl.
*C08G 59/00* (2006.01)
*C08G 64/34* (2006.01)
*C08G 64/20* (2006.01)

(52) U.S. Cl.
CPC .............. *C08G 64/34* (2013.01); *C08G 64/20* (2013.01)

(58) Field of Classification Search
CPC ....... C08G 64/34; C08G 64/0208; C07F 3/06; C07C 51/412; C07C 55/18; C07C 55/12
See application file for complete search history.

(56) References Cited

U.S. PATENT DOCUMENTS

| 4,981,948 | A | 1/1991 | Kawachi et al. |
| 5,026,676 | A | 6/1991 | Motika et al. |

(Continued)

FOREIGN PATENT DOCUMENTS

| CN | 102766039 A | 11/2012 |
| EP | 358326 * | 2/1989 .............. C08G 64/34 |

(Continued)

OTHER PUBLICATIONS

International Search Report, issued in PCT/KR2015/005951 (PCT/ISA/210), dated Aug. 31, 2015.

(Continued)

*Primary Examiner* — Shane Fang
(74) *Attorney, Agent, or Firm* — Birch, Stewart, Kolasch & Birch, LLP (57) ABSTRACT

An organic zinc catalyst having more uniform and fine particle size and showing more improved activity in a polymerization process for the preparation of a poly(alkylene carbonate) resin and a preparation method thereof, and a method of preparing a poly(alkylene carbonate) resin using the organic zinc catalyst, are provided. The preparation method of the organic zinc catalyst includes the steps of surface-treating a zinc precursor with a dispersant, and reacting the surface-treated zinc precursor with dicarboxylic acid to form a zinc dicarboxylate-based catalyst.

7 Claims, 2 Drawing Sheets

(56) References Cited

U.S. PATENT DOCUMENTS

| | | |
|---|---|---|
| 6,084,059 A | 7/2000 | Matsushita et al. |
| 7,405,265 B2 | 7/2008 | Moon et al. |
| 8,779,087 B2 | 7/2014 | Fujimoto et al. |
| 2005/0163971 A1* | 7/2005 | Kobayashi ............... G02B 1/04 428/156 |
| 2005/0272904 A1 | 12/2005 | Moon et al. |
| 2009/0240025 A1 | 9/2009 | Fujimoto et al. |
| 2012/0123066 A1 | 5/2012 | Fujimoto et al. |
| 2014/0200328 A1 | 7/2014 | Brym et al. |
| 2015/0361023 A1 | 12/2015 | Kim et al. |
| 2016/0194442 A1 | 7/2016 | Kim et al. |

FOREIGN PATENT DOCUMENTS

| | | |
|---|---|---|
| EP | 1 508 599 A1 | 2/2005 |
| EP | 1 558 665 A1 | 8/2005 |
| JP | 4708019 B2 | 6/2011 |
| JP | 5095954 B2 | 12/2012 |
| KR | 10-2003-0097236 A | 12/2003 |
| KR | 10-2003-0097237 A | 12/2003 |
| KR | 10-0722381 B1 | 5/2007 |
| KR | 10-2012-0023820 A | 3/2012 |
| KR | 10-2014-0062130 A | 5/2014 |
| WO | WO 99/51610 A1 | 10/1999 |
| WO | WO 2011/107577 A2 | 9/2011 |
| WO | WO 2013/034489 A1 | 3/2013 |

OTHER PUBLICATIONS

Meng et al., "Effects of the Structure and Morphology of Zinc Glutarate on the Fixation of Carbon Dioxide into Polymer", Journal of Polymer Science: Part A: Polymer Chemistry, vol. 40, pp. 3579-3591, 2002.

* cited by examiner

ORGANIC ZINC CATALYST, PREPARATION METHOD THEREOF, AND METHOD OF PREPARING POLY(ALKYLENE CARBONATE) RESIN USING THE SAME

CROSS-REFERENCE TO RELATED APPLICATION

This application claims the benefit of Korean Patent Application No. 10-2014-0072346 filed on Jun. 13, 2014, Korean Patent Application No. 10-2014-0072347 filed on Jun. 13, 2014, and Korean Patent Application No. 10-2015-0082527 filed on Jun. 11, 2015 with the Korean Intellectual Property Office, the disclosures of which are incorporated herein by reference in their entirety.

TECHNICAL FIELD

The present disclosure relates to an organic zinc catalyst having a more uniform and fine particle size and showing more improved activity in a polymerization process for the preparation of a poly(alkylene carbonate) resin and a preparation method thereof, and a method of preparing a poly(alkylene carbonate) resin using the organic zinc catalyst.

BACKGROUND OF ART

After the Industrial Revolution, humans established modern society while consuming huge amounts of fossil fuels which increases carbon dioxide concentration in the air, and the increase of the carbon dioxide concentration is further promoted by environmental destruction such as deforestation or the like. Since global warming is caused by an increase in greenhouse gases such as carbon dioxide, Freon, or methane in the air, it is important to decrease the concentration of carbon dioxide that significantly contributes to global warming, and various researches into emission regulations or stabilization of carbon dioxide have been conducted around the world.

Among them, a copolymerization reaction of carbon dioxide and an epoxide found by Inoue et al. has been expected to be a reaction capable of solving the global warming problem, and research has been actively conducted in view of using carbon dioxide as a carbon source as well as in view of chemical fixation of carbon dioxide. Particularly, a poly(alkylene carbonate) resin formed by polymerization of carbon dioxide and an epoxide has been recently spotlighted as a kind of biodegradable resin.

Various catalysts for preparing this poly(alkylene carbonate) resin have been studied and suggested in the past, and as a representative catalyst, a zinc dicarboxylate-based catalyst such as a zinc glutarate catalyst in which zinc and dicarboxylic acid are bonded to each other has been known.

The zinc dicarboxylate-based catalyst as described above, represented by the zinc glutarate catalyst, is formed by reacting a zinc precursor and a dicarboxylic acid such as glutaric acid with each other, and has a fine crystalline particle shape. However, it was difficult to control the zinc dicarboxylate-based catalyst having the crystalline particle shape to have a uniform and fine particle size during a preparation process thereof. The existing zinc dicarboxylate-based catalyst has a particle size of a nanometer scale, but an aggregate having an increased particle size and a decreased surface area is formed in a medium by aggregation of catalyst particles such that the activity may be deteriorated upon preparing the poly(alkylene carbonate) resin.

In this regard, it is known that as the zinc precursor used in the preparation of the zinc dicarboxylate-based catalyst has a smaller size, the produced catalyst has higher activity.

In general, zinc oxide powder used as a zinc source (zinc precursor) in the preparation of the zinc dicarboxylate-based catalyst is an ionic compound having a particle size of a few tens of nanometers to several hundred micrometers and a specific surface area of about 10 $m^2/g$. This zinc oxide powder is highly polar, and thus is dispersed well in polar solvents, but particles are aggregated with each other in polar solvents to form very large aggregates. When a catalytic synthetic reaction is allowed under the aggregation of particles, a non-uniform reaction occurs, and therefore heterogeneity in crystallinity of the resulting catalyst is increased to decrease activity of the catalyst, in view of the entire reaction system.

In this regard, International Patent Publication No. WO 2013/034489 and U.S. Pat. No. 7,405,265 disclose a method of increasing specific surface area of the zinc dicarboxylate-based catalyst by using an emulsifier or a non-ionic surfactant as a templating agent in a polar solution. However, the results of the previous literatures or studies showed that when zinc oxide and glutaric acid are used as a synthetic material of the zinc dicarboxylate-based catalyst, a catalyst synthesized in a non-polar solvent generally has higher activity than a catalyst synthesized in a polar solvent. Thus, there is still a limitation in the improvement of the catalytic activity by the method of using the polar solvent.

Further, International Patent Publication No. WO 2011/107577 discloses a method of synthesizing a catalyst after increasing a specific surface area of a zinc source used in the preparation of an organic zinc catalyst by surface treatment of the zinc source with organosilane. However, this method requires several steps (reaction, selection, drying, etc.) in the surface treatment of the zinc source with organosilane, and therefore there is a limitation in that this method is inefficient considering an improvement degree of the catalytic activity.

For this reaction, there is often a case that the existing known zinc dicarboxylate-based catalyst has a relatively large particle size and a non-uniform particle shape. However, when the zinc dicarboxylate-based catalyst having the above shape is applied to a polymerization process for preparing a poly(alkylene carbonate) resin, a sufficient contact area between a reactant and the catalyst is not secured, and therefore sufficient polymerization activity may not be exhibited. In addition, there is often a case that the activity of the existing zinc dicarboxylate-based catalyst itself is not satisfactory. Further, in the case of the zinc dicarboxylate-based catalyst, it is not easy to disperse and control the catalyst particles in a reaction solution due to non-uniformity of the particle size.

DETAILED DESCRIPTION OF THE INVENTION

Technical Problem

The present invention provides an organic zinc catalyst having more uniform and fine particle size and showing more improved activity in a polymerization process for the preparation of a poly(alkylene carbonate) resin, and a preparation method thereof.

Further, the present invention provides a method of preparing a poly(alkylene carbonate) resin using the organic zinc catalyst obtained by the above preparation method.

Technical Solution

According to the present invention, a preparation method of an organic zinc catalyst is provided, the preparation method including the steps of: surface-treating a zinc precursor with one or more dispersants selected from the group consisting of an anionic surfactant, a cationic surfactant, and an amphiphilic surfactant; and reacting the surface-treated zinc precursor with dicarboxylic acid having 3 to 20 carbon atoms to form a zinc dicarboxylate-based catalyst.

Further, according to the present invention, a zinc dicarboxylate-based catalyst obtained by reacting the zinc precursor, which is surface-treated with one or more dispersants selected from the group consisting of an anionic surfactant, a cationic surfactant, and an amphiphilic surfactant, with dicarboxylic acid having 3 to 20 carbon atoms, in which 0.001 to 5% by weight of the dispersant based on the weight of the catalyst is present on the catalyst, is provided.

Furthermore, according to the present invention, a method of preparing a poly(alkylene carbonate) resin is provided, the method including polymerizing monomers including an epoxide and carbon dioxide in the presence of the above-prepared organic zinc catalyst.

Hereinafter, a preparation method of an organic zinc catalyst, an organic zinc catalyst obtained by the preparation method, and a method of preparing a poly(alkylene carbonate) resin using the organic zinc catalyst according to exemplary embodiments of the present invention will be described in detail.

Unless particularly described in the present specification, technical terms are only used to describe a specific embodiment, and are not intended to limit the present invention. Singular forms used in the present specification include plural forms as long as they do not have clearly different meanings. The term 'including' used herein is to specify a specific property, region, integer, step, operation, factor, and/or component, but does not exclude presence or addition of another specific property, region, integer, step, operation, factor, component, and/or group.

Further, throughout the entire specification, a 'phosphate-based dispersant' refers to an arbitrary surfactant including a phosphate-based functional group having a P=O bond and a P—O bond (e.g., a phosphoric acid group or a phosphonic acid group) in the structure, in which one or more organic groups bind to the functional group.

I. Preparation Method of Organic Zinc Catalyst

According to an embodiment of the present invention, a preparation method of an organic zinc catalyst is provided, including the steps of:

surface-treating a zinc precursor with one or more dispersants selected from the group consisting of an anionic surfactant, a cationic surfactant, and an amphiphilic surfactant; and reacting the surface-treated zinc precursor with dicarboxylic acid having 3 to 20 carbon atoms to form a zinc dicarboxylate-based catalyst.

As a result of continuous studies of the present inventors, it was confirmed that when the zinc precursor is surface-treated with the dispersant and then the surface-treated zinc precursor is reacted with dicarboxylic acid in the preparation process of the organic zinc catalyst by reacting the zinc precursor and dicarboxylic acid, an organic zinc catalyst with improved activity may be obtained.

It is presumed that this effect is achieved because the surface-treated zinc precursor may maintain a fine and uniform dispersed state, regardless of polarity of a medium used in the preparation of the catalyst, and the surface-treated zinc precursor without aggregation is reacted with dicarboxylic acid to form active sites of the catalyst.

In particular, it was confirmed that the effect may be more favorably achieved when a dispersant having a phosphate-based functional group (e.g., phosphoric acid group, phosphonic acid group, etc.) is applied to the surface treatment of the zinc precursor. The reason is likely that a strong adhesive force (attractive force) acts between the phosphate-based functional group of the dispersant and the zinc precursor to give rise to steric hindrance, and therefore, the zinc precursors maintain the dispersed state without aggregation.

In addition, it is presumed that, due to the reaction progress of the catalyst preparation as described above, a risk that the zinc dicarboxylate-based catalyst particles will be aggregated with each other during the preparation process is decreased, such that more fine and uniform catalyst particles may be finally formed. Further, it is presumed that the zinc dicarboxylate-based catalyst particles having different crystalline characteristics from the previous catalysts are formed due to the reaction progress of the catalyst preparation as described above.

Therefore, as a result, it was confirmed that an organic zinc catalyst having superior activity may be obtained in a form of particles having more fine and uniform particle size. Further, it may be easier to disperse and control the catalyst particles in a reaction solution due to the fine and uniform particle size of the catalyst particle as described above. Therefore, the organic zinc catalyst may be very preferably applied to the preparation of a poly(alkylene carbonate) resin by the reaction of carbon dioxide and an epoxide.

Meanwhile, in the preparation method of the catalyst according to an embodiment, as the zinc precursor is surface-treated with the dispersant, aggregation of the zinc precursor in the medium may be minimized and the zinc precursor may have more improved dispersion stability, as compared to a zinc precursor that is not surface-treated with the dispersant. In addition, the surface-treated zinc precursor may maintain a fine, uniform, and stable dispersed state during the reaction with the dicarboxylic acid.

Hereinafter, respective steps that may be included in the preparation method of the organic zinc catalyst will be described in more detail.

(1) Surface-Treatment Step of Zinc Precursor

First, surface-treatment of the zinc precursor with the dispersant is performed.

This step is performed by mixing the zinc precursor and the dispersant in a solvent. That is, the step is a wet process, and the solvent in the step may be an arbitrary organic or aqueous solvent in which surface-treatment of the zinc precursor by the dispersant may be smoothly performed. An example of this solvent may include one or more solvents selected from the group consisting of toluene, hexane, dimethylformamide, ethanol, and water. In the case where a liquid medium is used in the reaction step of the zinc precursor and the dicarboxylic acid, following the surface-treatment step, it is preferable that the liquid medium has the same properties as those of the solvent used in the surface-treatment.

In addition, as the zinc precursor, any zinc precursor may be used without limitation as long as it has been previously used in the preparation of the zinc dicarboxylate-based catalyst, and a specific example of the zinc precursor may include one or more zinc compounds selected from the group consisting of zinc oxide (ZnO), zinc sulfate ($ZnSO_4$), zinc chlorate ($Zn(ClO_3)_2$), zinc nitrate ($Zn(NO_3)_2$), zinc acetate ($Zn(OAc)_2$), and zinc hydroxide ($Zn(OH)_2$).

The dispersant, which is a component capable of uniformly dispersing the zinc precursor without aggregation in the medium, may be one or more compounds selected from the group consisting of anionic surfactants, cationic surfactants, and amphiphilic surfactants. As the anionic surfactant, the cationic surfactant, and the amphiphilic surfactant, general compounds in the art to which the present invention pertains may be applied without particular limitation, respectively, and the dispersant may be suitably selected in consideration of the kinds, properties, or the like of the zinc precursor and medium used in the preparation of the zinc dicarboxylate-based catalyst.

Preferably, the dispersant may be a surfactant, in which a portion having an ionic functional group physically or chemically adsorbable onto the surface of the zinc precursor and a hydrocarbon portion highly compatible with the solvent co-exist in the molecule. The dispersant may be a surfactant having a structure of a copolymer, preferably, a block copolymer.

In particular, as the dispersant, a phosphate-based dispersant having a phosphate-based functional group may be preferably used. As the phosphate-based dispersant, one or more compounds selected from the group consisting of an anionic surfactant and an amphiphilic surfactant having a phosphoric acid group or a phosphonic acid group may be more preferably used. The phosphate-based dispersant is an arbitrary surfactant including a phosphate-based functional group having a P=O bond and a P—O bond (e.g., a phosphoric acid group, a phosphonic acid group, etc.) in the structure, in which one or more organic groups bind to the functional group. The phosphate-based functional group exhibits a strong adhesive force (attractive force) to the zinc precursor to give rise to a stable steric hindrance around the zinc precursor, and therefore the zinc precursors maintain the dispersed state without aggregation.

The dispersant may be used in an amount of 0.01 to 10% by weight, or 0.1 to 10% by weight, or 1 to 10% by weight, or 1 to 7.5% by weight, or 1 to 5% by weight, with respect to the zinc precursor. That is, for sufficient surface treatment of the zinc precursor, it is preferable that the dispersant is mixed in an amount of 0.01% by weight with respect to the zinc precursor. However, in the case where the dispersant is excessively mixed, the dispersant may participate in the reaction to cause a side reaction or to affect a composition of the medium, thereby deteriorating a crystalline property of the catalyst. As a result, aggregation of the zinc precursor may be induced. Therefore, it is preferable that the dispersant is used in an amount of 10% by weight or less with respect to the zinc precursor.

According to a specific embodiment, the zinc precursor surface-treated with the dispersant as described above may have a $D_{90}$ particle size distribution of 10 μm or less, 1 to 10 μm, 1.5 to 8 μm, or 3 to 7.5 μm, as measured in an ethanol solvent. $D_{90}$ represents a particle size at which an accumulated volume is 90% of the total volume of particles when particles are accumulated from particles having a small particle size, and here, the particle size of the surface-treated zinc precursor means a diameter of the aggregate formed by aggregation between the zinc precursors in a state in which the zinc precursor is added to the medium for reaction with dicarboxylic acid.

As the zinc precursor is surface-treated with the dispersant, particle size distribution may be stably maintained during the reaction with the dicarboxylic acid. However, in the case of using a zinc precursor having a $D_{90}$ particle size distribution of larger than 10 μm in the reaction with the dicarboxylic acid, it is difficult to uniformly perform the reaction with the dicarboxylic acid, and the zinc precursor is precipitated before completion of the reaction, and therefore a stable dispersion state may not be maintained.

(2) Reaction Step of Surface-Treated Zinc Precursor and Dicarboxylic Acid

Meanwhile, the step of reacting the surface-treated zinc precursor with dicarboxylic acid to form the zinc dicarboxylate-based catalyst is performed.

As the dicarboxylic acid, an arbitrary dicarboxylic acid having 3 to 20 carbon atoms may be used. Specifically, the dicarboxylic acid may be an aliphatic dicarboxylic acid such as malonic acid, glutaric acid, succinic acid, and adipic acid, or an aromatic dicarboxylic acid such as terephthalic acid, isophthalic acid, homophthalic acid, and phenyl glutaric acid. Otherwise, various aliphatic or aromatic dicarboxylic acids having 3 to 20 carbon atoms may be used. In view of the activity of the catalyst, it is preferable that the dicarboxylic acid is glutaric acid. In this case, the organic zinc catalyst is a zinc glutarate-based catalyst.

According to an embodiment of the present invention, the dicarboxylic acid may be used in an amount of moles equivalent to or excessively higher than the amount of the zinc precursor, and more specifically, the dicarboxylic acid may be used in an amount of about 1 mol to about 1.5 mol, or about 1.1 mol to about 1.3 mol, based on 1 mol of the zinc precursor. When the reaction is performed using dicarboxylic acid in an amount equivalent to or excessively higher than the amount of the zinc precursor, the reaction may occur slowly while the uniformly dispersed zinc precursors are surrounded by dicarboxylic acid molecules or ions. Therefore, zinc precursors may react with dicarboxylic acids while zinc precursors hardly aggregate with each other, and therefore an organic zinc catalyst having a more uniform and fine particle size and showing improved activity may be obtained.

The reaction step may be performed in a liquid medium in which reactants including the surface-treated zinc precursor and the dicarboxylic acid exist (for example, in a state of a solution or dispersion in which the reactants are dissolved or dispersed).

In this regard, the reaction may be performed while adding a solution or dispersion containing the surface-treated zinc precursor in portions two times or more to a solution or dispersion containing the dicarboxylic acid.

That is, some of the solution or dispersion containing the surface-treated zinc precursor is primarily injected to the solution or dispersion containing the dicarboxylic acid to perform the reaction, and then the rest of the reaction is performed while adding the rest of the solution or dispersion containing the surface-treated zinc precursor in portions.

Therefore, the entire reaction step may be performed while maintaining the molar ratio of the zinc precursor and dicarboxylic acid in the reaction system, and the organic zinc catalyst having a more uniform and fine particle size and improved activity may be obtained. Further, the entire reaction step may be performed while uniformly dripping the solution or dispersion containing the surface-treated zinc precursor in a droplet form into the solution or dispersion containing the dicarboxylic acid.

In addition, the step of reacting the surface-treated zinc precursor and the dicarboxylic acid may be performed in the liquid medium. As the liquid medium, any organic or aqueous solvent known to uniformly dissolve or disperse the surface-treated zinc precursor and/or the dicarboxylic acid may be used. A specific example of the liquid medium may include one or more solvents selected from the group consisting of toluene, hexane, dimethylformamide, ethanol, and water.

The reaction of the surface-treated zinc precursor and the dicarboxylic acid may be performed at about 50 to 130° C. for about 1 h to about 10 h. As described above, the surface-treated zinc precursor is added in portions at the same time interval during the entire reaction time, and the molar ratio of the reactants in the reaction system may be maintained throughout the entire reaction step.

If necessary, a process of washing and drying the synthesized organic zinc catalyst may be performed.

II. Organic Zinc Catalyst

According to another aspect of the present invention, an organic zinc catalyst obtained by reacting the zinc precursor, which is surface-treated with one or more dispersants selected from the group consisting of an anionic surfactant, a cationic surfactant, and an amphiphilic surfactant, with dicarboxylic acid having 3 to 20 carbon atoms, in which 0.001 to 5% by weight of the dispersant based on the weight of the catalyst is present on the catalyst is provided.

The organic zinc catalyst may be obtained by reacting the zinc precursor, which is surface-treated with the dispersant, and dicarboxylic acid, and preferably, by the above-described preparation method.

That is, the organic zinc catalyst is prepared through reaction with dicarboxylic acid in a state in which the surface-treated zinc precursor is optimally dispersed.

Therefore, the organic zinc catalyst according to an embodiment of the present invention may be in a form of uniform particles having an average particle size of about 0.5 μm or less, or about 0.1 μm to about 0.4 μm, or about 0.2 μm, as compared to an organic zinc catalyst prepared by using non-surface-treated zinc precursor according to the existing method (for example, a general organic zinc catalyst having a primary particle size of about 1 to 2 μm).

Here, the 'primary particle size' of the catalyst means a size of a catalyst particle itself in a state in which the catalyst is not mixed with a medium, and the primary particle size may be determined by electron microscopy. Further, a 'secondary particle size' of the catalyst means a size of an aggregate formed by aggregation of the catalyst particles in a state in which the catalyst is mixed with the medium.

In addition, as the organic zinc catalyst has a fine and uniform particle size, the organic zinc catalyst may have a surface area that is increased by about 1.5 times to about 6 times, compared to a surface area of the general organic zinc catalyst (for example, about 1.1 to 1.3 m$^2$/g).

Further, the dispersant used for surface treatment of the zinc precursor may contribute to improving dispersibility of the finally produced organic zinc catalyst as well as dispersibility of the zinc precursor.

That is, the zinc precursor surface-treated with the dispersant reacts with the dicarboxylic acid to form the organic zinc catalyst, and a portion of the dispersant separated during this process stabilizes the finally produced organic zinc catalyst.

Therefore, at the time of measuring the particle size (secondary particle size) of the organic zinc catalyst in the presence of an ethanol solvent, the organic zinc catalyst may have a $D_{50}$ particle size distribution of 5 μm or less, 1 to 5 μm, 1 to 3 μm, or 1 to 5.5 μm. $D_{50}$ represents a particle size at which an accumulated volume reaches 50% of the total volume of particles when particles are accumulated from particles having a small particle size.

Further, 5% by weight or less, or 0.001 to 5% by weight, or 0.001 to 3% by weight, or 0.01 to 1.5% by weight of the dispersant based on the weight of the catalyst may be present on the organic zinc catalyst.

In the case where the dispersant is excessively present on the catalyst, the dispersant may block an active surface of the catalyst to decrease the activity of the catalyst. Further, in the case where the dispersant is excessively present on the catalyst, a molecular weight of a poly(alkylene carbonate) resin may be decreased or side reactions may be induced during preparation of the resin using the catalyst, thereby decreasing productivity. Therefore, it is preferable that the content of the dispersant present on the catalyst is 5% by weight or less based on the weight of the catalyst.

In this regard, it is known that in order to improve dispersibility of a general organic zinc catalyst upon preparing a poly(alkylene carbonate) resin, a dispersant should be used at a degree in which a dispersant layer having a thickness of 10 nm or more may be formed on the surface of the catalyst.

For example, theoretically, in order to form a dispersant layer having a thickness of 10 nm (assuming a density is about 1 g/cm$^3$) on a surface of a general zinc glutarate catalyst (density of about 2.1 g/cm$^3$) having a surface area of 10 to 20 m$^2$/g, 10 to 25% by weight of the dispersant should be used based on the weight of the catalyst.

On the contrary, as the organic zinc catalyst according to an embodiment of the present invention is prepared by the above-mentioned method, the catalyst has an improved surface area, compared to that of a previous catalyst, and stable dispersibility of the catalyst may be secured even with 5% by weight or less of the dispersant, based on the weight of the zinc precursor used in the synthesis of the catalyst.

This amount is significantly smaller than an amount of the theoretically required dispersant (10 to 25% by weight, based on the weight of the catalyst), and corresponds to a significantly smaller amount in consideration of the improved surface area.

Therefore, when the organic zinc catalyst is used in the preparation of a poly(alkylene carbonate) resin by copolymerization of carbon dioxide and an epoxide, contact areas between the catalyst particles and reactants may be further increased, and therefore improvement in the activity may be expected.

III. Preparation Method of Poly(Alkylene Carbonate) Resin Using the Catalyst

According to another embodiment of the present invention, a preparation method of a poly(alkylene carbonate) resin is provided, including the step of polymerizing monomers containing an epoxide and carbon dioxide in the presence of the organic zinc catalyst prepared by the above-described method.

In the preparation method of the resin, the organic zinc catalyst may be used in a form of a non-uniform catalyst, and the polymerizing step may be performed by solution polymerization in an organic solvent. Therefore, reaction heat may be suitably controlled, and it may be easy to control a molecular weight or viscosity of a desired poly(alkylene carbonate) resin.

In this solution polymerization, as the solvent, one or more selected from the group consisting of methylene chloride, ethylene dichloride, trichloroethane, tetrachloroethane, chloroform, acetonitrile, propionitrile, dimethylformamide, N-methyl-2-pyrrolidone, dimethyl sulfoxide, nitromethane, 1,4-dioxane, hexane, toluene, tetrahydrofuran, methylethyl ketone, methylamineketone, methyl isobutyl ketone, acetone, cyclohexanone, trichloroethylene, methyl acetate, vinyl acetate, ethyl acetate, propyl acetate, butyrolactone, caprolactone, nitropropane, benzene, styrene, xylene, and methyl propasol may be used. Using them, when methylene chloride or ethylene dichloride is used as the solvent, a polymerization reaction may be more effectively performed.

The solvent may be used at a weight ratio of about 1:0.5 to 1:100, and preferably about 1:1 to 1:10, based on the epoxide. In this regard, if the ratio is excessively low as less than about 1:0.5, the solvent does not suitably serve as a reaction medium, and therefore it may be difficult to implement advantages of the solution polymerization. Further, if the ratio is more than about 1:100, a concentration of the epoxide or the like may be relatively decreased, and therefore a molecular weight of a finally formed resin may be decreased, or side reactions may be increased.

In addition, the organic zinc catalyst may be injected at a molar ratio of about 1:50 to 1:1000, based on the epoxide. More preferably, the organic zinc catalyst may be injected at a molar ratio of about 1:70 to about 1:600, or about 1:80 to about 1:300, based on the epoxide. If the ratio is excessively small, it is difficult to obtain sufficient catalytic activity upon solution polymerization. On the contrary, if the ratio is excessively large, an excessive amount of catalyst is used, which is not efficient, and by-products may be formed, or back-biting of the resin may occur due to heating in the presence of the catalyst.

Meanwhile, as the epoxide, one or more selected from the group consisting of: alkylene oxides having 2 to 20 carbon atoms, substituted or unsubstituted with a halogen or an alkyl group having 1 to 5 carbon atoms; cycloalkylene oxides having 4 to 20 carbon atoms, substituted or unsubstituted with a halogen or an alkyl group having 1 to 5 carbon atoms; and styrene oxides having 8 to 20 carbon atoms substituted or unsubstituted with a halogen or an alkyl group having 1 to 5 carbon atoms may be used. As a representative epoxide, an alkylene oxide having 2 to 20 carbon atoms, substituted or unsubstituted with a halogen or an alkyl group having 1 to 5 carbon atoms, may be used.

Specific examples of the epoxide may include ethylene oxide, propylene oxide, butene oxide, pentene oxide, hexene oxide, octene oxide, decene oxide, dodecene oxide, tetradecene oxide, hexadecene oxide, octadecene oxide, butadiene monoxide, 1,2-epoxy-7-octene, epifluorohydrin, epichlorohydrin, epibromohydrin, isopropyl glycidyl ether, butyl glycidyl ether, t-butyl glycidyl ether, 2-ethylhexyl glycidyl ether, allyl glycidyl ether, cyclopentene oxide, cyclohexene oxide, cyclooctene oxide, cyclododecene oxide, alpha-pinene oxide, 2,3-epoxynorbornene, limonene oxide, dieldrin, 2,3-epoxypropylbenzene, styrene oxide, phenylpropylene oxide, stilbene oxide, chlorostilbene oxide, dichlorostilbene oxide, 1,2-epoxy-3-phenoxypropane, benzyloxymethyl oxirane, glycidyl-methylphenyl ether, chlorophenyl-2,3-epoxypropyl ether, epoxypropyl methoxyphenyl ether, biphenyl glycidyl ether, glycidyl naphthyl ether, and the like. As the most representative epoxide, ethylene oxide is used.

In addition, the above-mentioned solution polymerization may be performed at about 50° C. to about 100° C. and at about 15 bar to about 50 bar for about 1 h to about 60 h. Further, the solution polymerization may be more preferably performed at about 70° C. to about 90° C. and at about 20 bar to about 40 bar for about 3 h to about 40 h.

Since other polymerization processes and conditions except for the above-mentioned contents may depend on general polymerization conditions for preparing a poly(alkylene carbonate) resin, a detailed description thereof will be omitted.

Advantageous Effects

According to the present invention, a preparation process of a catalyst is optimized, thereby preparing and providing an organic zinc catalyst showing a more fine and uniform particle size and excellent activity, which is used for the preparation of a poly(alkylene carbonate) resin.

DETAILED DESCRIPTION OF THE EMBODIMENTS

Hereinafter, preferred examples of the present invention will be provided for better understanding of the present invention. It is to be understood that the following examples are only for illustrative purposes and are not intended to limit the present invention.

Example 1

In a 250 mL round bottom flask, 75 ml of toluene, 50 mmol of ZnO powder, and 2% by weight of a phosphate-based anionic surfactant represented by the following formula (Crodafos CS2A, manufactured by CRODA) based on ZnO were added, and vigorously stirred at room temperature for 20 min to prepare a surface-treated ZnO dispersed solution (ZnO dispersion).

(n = 1 or n = 2)

50 mmol of glutaric acid was added to the ZnO dispersion at room temperature, and then the temperature was raised to 60° C., followed by reaction under vigorous stirring for 10 h.

Thereafter, the reaction vessel was cooled to room temperature, and a precipitate was separated by filtration. The separated precipitate was washed with acetone three times or more. The washed precipitate was dried in a vacuum oven at 85° C. for 12 h, and finally, 9.3 g of a zinc glutarate (ZnGA) catalyst was obtained (yield of about 95%).

Example 2

9.2 g of a ZnGA catalyst (yield of about 94%) was obtained in the same manner as in Example 1, except that a cationic surfactant (DISPERBYK-163, manufactured by BYK; amine value of 10 mg KOH/g, density of 0.99 g/ml at 20° C.) was used instead of the phosphate-based anionic surfactant during the preparation of the ZnO dispersion.

Example 3

8.8 g of a ZnGA catalyst (yield of about 90%) was obtained in the same manner as in Example 1, except that a phosphate-based amphiphilic surfactant (DISPERBYK-180, manufactured by BYK; amine value of 94 mg KOH/g, acid value of 94 mg KOH/g, density of 1.08 g/ml at 20° C.) was used instead of the phosphate-based anionic surfactant during the preparation of the ZnO dispersion.

Example 4

9.2 g of a ZnGA catalyst (yield of about 94% was obtained in the same manner as in Example 1, except that a phosphate-based anionic surfactant (DISPERBYK-102, manufactured by BYK; poly(oxy-1,2-ethanediyl), alpha-isotridecyl-omega-hydroxy-, phosphate, potassium salt; acid value of 101 mg KOH/g, density of 1.06 g/ml at 20° C.) was used during the preparation of the ZnO dispersion.

Example 5

9.3 g of a ZnGA catalyst (yield of about 95%) was obtained in the same manner as in Example 1, except that a phosphate-based anionic surfactant (D1544, manufactured by TCI; di(polyethylene glycol 4-nonylphenyl) phosphate) was used during the preparation of the ZnO dispersion.

Comparative Example 1

In a 250 mL round bottom flask, 75 ml of toluene, 50 mmol of ZnO, and 50 mmol of glutaric acid were added, and then the temperature was raised to 60° C., followed by reaction under vigorous stirring for 10 h. Thereafter, the reaction vessel was cooled to room temperature, and a precipitate was separated by filtration. The separated precipitate was washed with acetone three times or more. The washed precipitate was dried in a vacuum oven at 85° C. for 12 h, and finally, 9.5 g of a ZnGA catalyst was obtained (yield of about 97%).

Comparative Example 2

9.1 g of a ZnGA catalyst (yield of about 93%) was obtained in the same manner as in Example 1, except that a non-ionic surfactant (Pluronic P-123, manufactured by BASF) represented by the following formula was used instead of the phosphate-based anionic surfactant during the preparation of the ZnO dispersion.

Comparative Example 3

9.1 g of a ZnGA catalyst (yield of about 93%) was obtained in the same manner as in Example 1, except that a non-ionic surfactant (Briji58, manufactured by Sigma-Aldrich) represented by the following Formula was used instead of the phosphate-based anionic surfactant during the preparation of the ZnO dispersion.

Comparative Example 4

9.4 g of a ZnGA catalyst (yield of about 96%) was obtained in the same manner as in Comparative Example 1, except that a phosphate-based anionic surfactant (Crodafos CS2A, manufactured by CRODA) was injected at the time of completing the reaction of ZnO and glutaric acid.

Experimental Example 1

(Particle Size Analysis of Zinc Precursor and Organic Ainc Catalyst)

Figure 1:
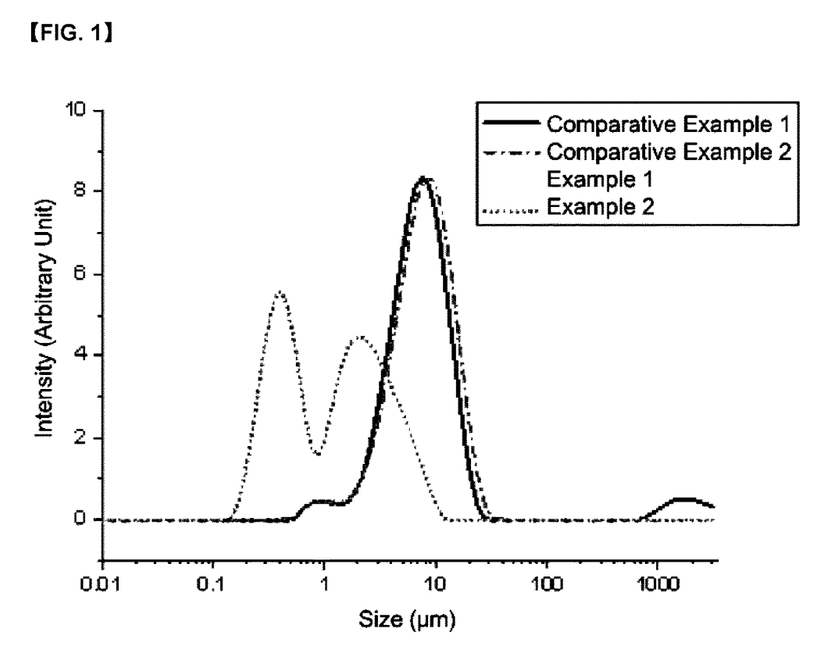
FIG. 1 is a graph showing the results of particle size analysis of zinc precursors used in the preparation of catalysts of examples and comparative examples.

With respect to the ZnO dispersions used in the examples and ZnO or ZnO dispersions used in the comparative examples, particle size distribution of ZnO was analyzed in an ethanol solvent using a particle size analyzer (MASTERSIZER 3000). The results are given in the following Table 1 and FIG. 1.

In the same manner as above, particle size analysis of the organic zinc catalysts (ZnGA) prepared in the examples and comparative examples was also performed, and the results are given in Table 1.

Experimental Example 2

(Measurement of Residual Amount of Dispersant)

After termination of the catalytic synthetic reaction, a filtrate was collected, and the weight of the filtered dispersant under vacuum was measured. The weight of the dispersant detected in the filtrate was subtracted from the weight of the dispersant injected to the catalytic synthetic reaction to calculate the residual amount of the dispersant present on the surface of the organic zinc catalyst. The residual amount of the dispersant was converted into a percentage of the weight of the catalyst, and is given in the following Table 1.

Experimental Example 3

(Evaluation of Dispersion Stability by Measurement of Sedimentation Rate of Zinc Precursor)

In the examples and comparative examples, before the reaction of ZnO and glutaric acid, a dispersion stability tester, LumiSizer, was used to measure sedimentation rates of zinc dispersion or ZnO particles in the reaction solution. The sedimentation rate was determined as a rate at which the particles in the solution move towards the bottom of a container under a centrifugal force of 5 G. The results are given in the following Table 1.

Experimental Example 4

(Analysis of Chemical Composition of Catalyst)

Figure 2:
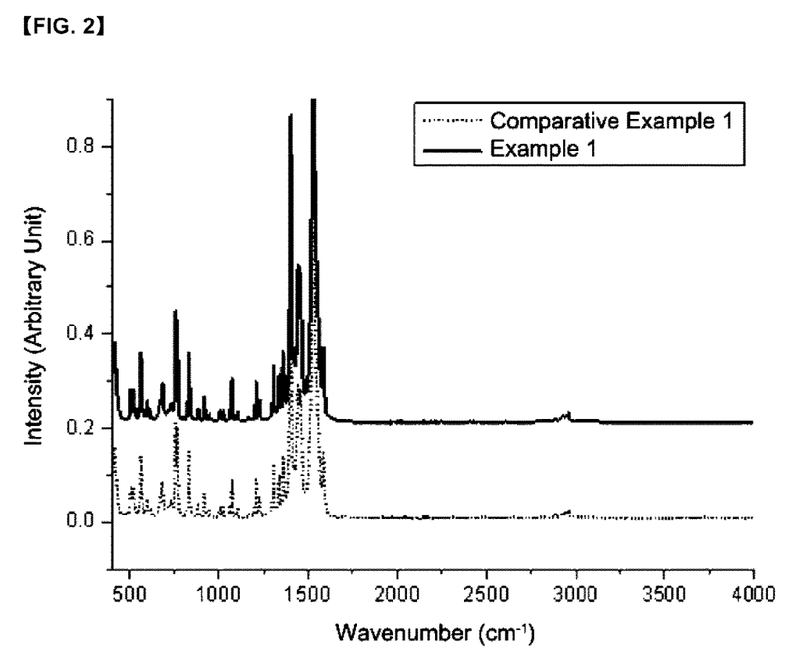
FIG. 2 is a graph showing the results of measuring IR spectroscopy of the catalysts obtained in examples and comparative examples.

In order to examine whether the surfactant used in the surface-treatment of the zinc precursor chemically affects the catalyst, chemical compositions of the ZnGA catalysts obtained in Example 1 and Comparative Example 1 were analyzed by IR spectroscopy, and the results are given in FIG. 2.

Referring to FIG. 2, the ZnGA catalysts according to Example 1 and Comparative Example 1 showed identical peak patterns, indicating that catalysts having the same composition were synthesized.

Experimental Example 5

(Measurement of Phosphorus (P) Content in Catalyst)

After acid digestion of the ZnGA catalysts obtained in Example 1 and Comparative Example 1, the contents of phosphorus (P) in the samples were measured using an ICP-OES (Optima 7300DV) device twice, and a mean value was calculated.

As a result, the catalyst of Example 1 was found to include phosphorus of about 510 mg-P/kg-catalyst, and the catalyst of Comparative Example 1 was found to include phosphorus of less than 0.5 (<0.5) mg-P/kg-catalyst. That is, in the catalyst of Example 1 which was prepared by using the dispersant having a phosphate-based functional group, about 0.05% by weight of phosphorus (P) remained. When this content is converted into the weight of the dispersant, it is about 0.7 to 1.2% by weight, which is a similar result to that of Experimental Example 2.

Experimental Example 6

(Preparation of Poly(Ethylene Carbonate))

Poly(ethylene carbonate) (PEG) was prepared using the ZnGA catalysts of the examples and comparative examples by the following method.

In a glove box, 0.2 g of a ZnGA catalyst and 8.52 g of dichloromethane were put into a high pressure reactor, and 8.9 g of ethylene oxide was added thereto. Thereafter, the reactor was pressurized to 30 bar using carbon dioxide. A polymerization reaction was performed at 70° C. for 3 h. After the reaction was terminated, unreacted carbon dioxide and ethylene oxide were removed together with a solvent dichloromethane. In order to confirm an amount of the prepared PEC, the remaining solid was completely dried and then weighed. Activities and yields of the catalysts according to the polymerization results are given in the following Table 1.

TABLE 1

|  | $D_{90}$ of ZnO (μm) | Sedimentation rate (μm/s) | Residual amount of dispersant (%) | $D_{10}$ of ZnGA (μm) | $D_{50}$ of ZnGA (μm) | $D_{90}$ of ZnGA (μm) | Activity of catalyst (g-PEC/g-ZnGA) |
|---|---|---|---|---|---|---|---|
| Example 1 | 3.64 | 1.85 | 1.2 | 0.35 | 1.36 | 4.37 | 46 |
| Example 2 | 4.98 | 2.14 | 0.9 | 0.57 | 2.12 | 6.53 | 32 |
| Example 3 | 5.07 | 2.20 | 1.3 | 0.60 | 2.34 | 7.29 | 34 |
| Example 4 | 4.45 | 2.18 | 1.2 | 0.38 | 1.51 | 4.61 | 36 |
| Example 5 | 4.66 | 2.04 | 1.3 | 0.44 | 1.66 | 5.23 | 41 |
| Comparative Example 1 | 11.5 | too fast | — | 3.14 | 12.8 | 38.62 | 23 |
| Comparative Example 2 | 11.4 | too fast | 0.8 | 4.36 | 17.8 | 57.2 | 27 |
| Comparative Example 3 | 12.2 | too fast | 1.0 | 4.99 | 19.50 | 57.55 | 21 |
| Comparative Example 4 | 11.5 | too fast | 0.8 | 2.82 | 11.50 | 34.69 | 20 |

Referring to Table 1, in Comparative Example 1 using the non-surface-treated zinc precursor and in Comparative Examples 2 and 3 using the zinc precursor surface-treated with the non-ionic surfactant, zinc precursors were aggregated in the solvent and many particles having a particle size of more than 10 μm were observed. Further, the catalysts prepared by using these zinc precursors in the comparative examples were found to have low catalytic activity (polymerization yield).

In contrast, in the examples, aggregation of the zinc precursor was remarkably reduced, and therefore catalysts prepared by using these zinc precursors were found to have a more fine and uniform size and high activity.

The invention claimed is:

1. A preparation method of an organic zinc catalyst, the method comprising the steps of:
    surface-treating a zinc precursor by mixing the zinc precursor and a dispersant in a solvent; and
    reacting the surface-treated zinc precursor with dicarboxylic acid having 3 to 20 carbon atoms to form a zinc dicarboxylate-based catalyst,
    wherein the dispersant is a phosphate-based dispersant having a phosphoric acid group or a phosphonic acid group,
    wherein the dispersant is one or more dispersants selected from the group consisting of an anionic surfactant, a cationic surfactant, and an amphiphilic surfactant,
    wherein the solvent is one or more selected from toluene, hexane and dimethylformamide, wherein the surface-treated zinc precursor has a $D_{90}$ particle size distribution of 10 μm or less, as measured in an ethanol solvent.

2. The preparation method of claim 1, wherein the dispersant is one or more compounds selected from the group consisting of an anionic surfactant and an amphiphilic surfactant having a phosphoric acid group or a phosphonic acid group.

3. The preparation method of claim 1, wherein the dispersant is mixed in an amount of 0.01 to 10% by weight, based on the zinc precursor.

4. The preparation method of claim 1, wherein the zinc precursor is one or more zinc compounds selected from the group consisting of zinc oxide (ZnO), zinc sulfate ($ZnSO_4$), zinc chlorate ($Zn(ClO_3)_2$), zinc nitrate ($Zn(NO_3)_2$), zinc acetate ($Zn(OAc)_2$), and zinc hydroxide ($Zn(OH)_2$).

5. The preparation method of claim 1, wherein the dicarboxylic acid is one or more compounds selected from the group consisting of malonic acid, glutaric acid, succinic acid, adipic acid, terephthalic acid, isophthalic acid, homophthalic acid, and phenyl glutaric acid.

6. The preparation method of claim 1, wherein the reaction of the surface-treated zinc precursor and dicarboxylic acid is performed in the presence of reactants of 1 to 1.5 mol of the dicarboxylic acid, based on 1 mol of the surface-treated zinc precursor.

7. The preparation method of claim 1, wherein the reaction of the surface-treated zinc precursor and dicarboxylic acid is performed in one or more liquid media selected from the group consisting of toluene, hexane, dimethylformamide, ethanol, and water.

* * * * *